United States Patent [19]
Owens et al.

[11] Patent Number: 6,153,644
[45] Date of Patent: Nov. 28, 2000

[54] STABILIZED INJECTABLE PHARMACEUTICAL COMPOSITIONS CONTAINING TAXOID ANTI-NEOPLASTIC AGENTS

[75] Inventors: Walter H. Owens, Star City; Timothy A. Irby, Morgantown, both of W. Va.

[73] Assignee: Mylan Pharmaceuticals, Inc., Morgantown, W. Va.

[21] Appl. No.: 09/432,084

[22] Filed: Nov. 2, 1999

Related U.S. Application Data

[62] Division of application No. 09/203,350, Dec. 2, 1998, Pat. No. 6,071,952.

[51] Int. Cl.[7] .................................................. A61K 31/335
[52] U.S. Cl. ............... 514/449; 252/186.25; 252/188.28; 252/363.5; 252/364; 252/403; 252/407; 514/772; 514/785; 514/769; 514/970; 514/973
[58] Field of Search .................. 252/186.25, 188.28, 252/363.5, 364, 403, 407; 514/449, 772, 785, 769, 970, 973

[56] References Cited

U.S. PATENT DOCUMENTS

| | | |
|---|---|---|
| 5,403,858 | 4/1995 | Bastard et al. . |
| 5,438,072 | 8/1995 | Bobee et al. . |
| 5,462,726 | 10/1995 | Lodge ..................................... 514/558 |
| 5,504,102 | 4/1996 | Agharkar et al. . |
| 5,670,536 | 9/1997 | Durr et al. . |
| 5,681,846 | 10/1997 | Trissel ..................................... 514/449 |
| 5,698,582 | 12/1997 | Bastart et al. . |
| 5,714,512 | 2/1998 | Bastart et al. . |
| 5,733,888 | 3/1998 | Carver et al. . |

OTHER PUBLICATIONS

Derwent Abstract 93–309115, "Anticancer Pharmaceutical Composition" (Aug., 1993).

*Primary Examiner*—Frederick Krass
*Attorney, Agent, or Firm*—Rothwell, Figg, Ernst & Manbeck

[57] ABSTRACT

A stabilized, injectable pharmaceutical composition for human administration comprises (a) an antineoplastic compound, (b) a solubilizing/dispersing agent, and (c) a stabilizing amount of an anti-oxidant.

5 Claims, 1 Drawing Sheet

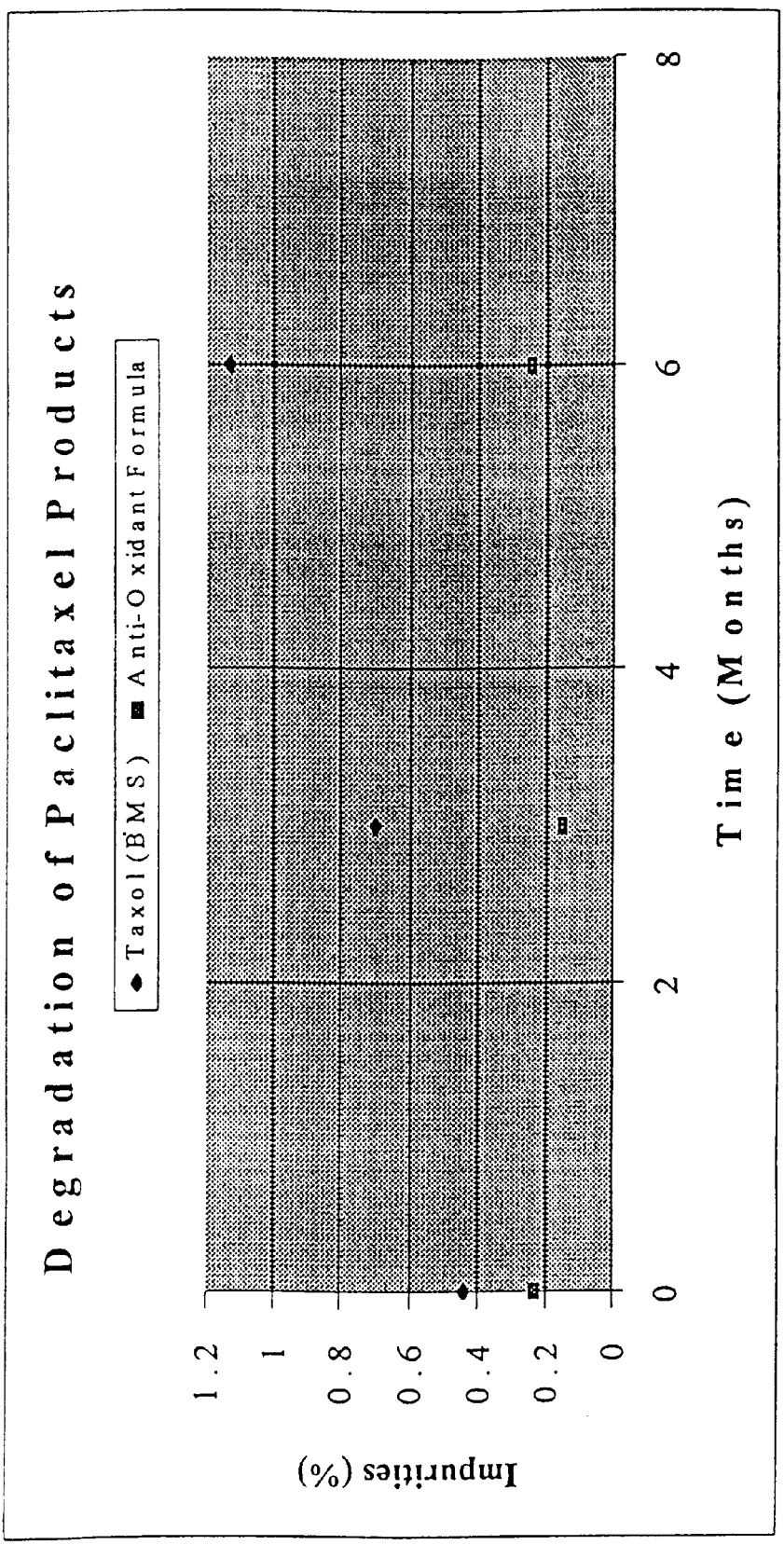
Figure I. Degradation of Paclitaxel Products.

STABILIZED INJECTABLE PHARMACEUTICAL COMPOSITIONS CONTAINING TAXOID ANTI-NEOPLASTIC AGENTS

This application is a divisional of U.S. Ser. No. 09/203,350, filed Dec. 2, 1998, now U.S. Pat. No. 6,071,952.

BACKGROUND OF INVENTION

1. Field of the Invention

The present invention relates generally to the field of cancer treatment. More particularly, the invention relates to anti-neoplastic injectable pharmaceutical compositions with enhanced stability.

2. Description of the Related Art

Various methods of stabilizing injectable pharmaceutical compositions containing taxoid anti-neoplastic agents have been disclosed. One method, disclosed in U.S. Pat. No. 5,504,102 to Bristol-Myers Squibb Company, deals with the treatment of Cremophor EL (a commercially available polyoxyethylated castor oil supplied by BASF) to be used in an injectable paclitaxel (an anti-neoplastic compound) pharmaceutical composition. The patent discloses the treatment of Cremophor EL with alumina or sufficient acid to reduce the level of carboxylate anions. According to the patent, carboxylate anions originate from the production of Cremophor EL and catalyze the degradation of paclitaxel. Although the mineral acid treatment and further processing of Cremophor EL yield substantially better stability than if the injectable were manufactured without an acid stabilizing agent for short-term storage conditions (i.e., 50° C. for approximately 2 months), long-term stability studies (i.e., 40° C./75% relative humidity for 6 months) indicate that paclitaxel is still susceptible to degradation. In addition, the mineral acid treatment strategy must be tightly controlled in order that the pH of the formulation, during manufacturing as well as in the finished dosage form, does not reach a level in which paclitaxel will decompose due to acid catalyzed hydrolysis mechanisms.

A second method for preventing paclitaxel degradation is disclosed in U.S. Pat. No. 5,733,888 to NaPro BioTheraputics Inc. According to this method, paclitaxel degradation is controlled by maintaining the pH of the finished formulation at or below a value of seven (7). The pH of the formulation can be adjusted by treating the Cremophor EL with an acid. The patent discloses that acids in powder form are preferred over those which contain water. Water is most likely avoided since in the presence of acids, water provides a vehicle as well as a reagent for acid catalyzed hydrolysis of paclitaxel, even at moderately acidic pH levels. Again, this type of treatment technology of the Cremophor EL must be tightly controlled in order to guard against pH deviations which could lead to hydrolytic degradation of the taxoid compound.

Other pharmaceutical formulations of taxoid compounds exist in which long-term shelf life is problematic. Several U.S. patents have been assigned to Rhone-Poulenc Rorer (U.S. Pat. No. 5,403,858, U.S. Pat. No. 5,438,072, U.S. Pat. No. 5,670,536, U.S. Pat. No. 5,698,582, U.S. Pat. No. 5,714,512) which address a formulation composed of a taxane compound dissolved in a surfactant selected from a group consisting of polysorbate, polyoxyethylene glycol, or hydrogenated castor oil, and essentially free of ethanol. Although reduction of ethanol has a therapeutic advantage, stability of these formulations is suspect. This is demonstrated by the directed storage of these products under refrigerated conditions.

Reduced long-term shelf life leads to increased manufacturing costs due to extensive consumption of raw materials and yields a product of inferior quality, both translating into higher costs to the patient. Therefore, a stabilization strategy is needed to prevent the degradation of taxoid anti-neoplastic compounds in injectable pharmaceutical compositions independent of the injectable solvent system.

SUMMARY OF INVENTION

In accordance with the present invention, an injectable pharmaceutical composition for human administration comprising (a) an anti-neoplastic compound, (b) a solubilizing/dispersing agent, and (c) a stabilizing amount of an anti-oxidant is disclosed.

The manufacturing techniques of the pharmaceutical preparations of this invention are straightforward and employ conventional manufacturing equipment. The compositions of this invention are stable during long-term storage.

BRIEF DESCRIPTION OF DRAWINGS

The invention is further illustrated by the accompanying drawing, in which:

FIG. 1 illustrates a graphical representation of the relative impurity levels for Taxol® and for the anti-oxidant stabilized formulation of the present invention for a period of six (6) months at 40° C./75% Relative Humidity. The slopes of these curves represent the decomposition rate of the two formulas.

DETAILED DESCRIPTION OF THE INVENTION

The injectable pharmaceutical preparations of this invention comprise an anti-neoplastic compound, a dispersing/solubilizing agent, and a stabilizing amount of an anti-oxidant. As used herein, "anti-neoplastic compound" refers to taxoids and those compounds which are structurally similar to the taxoid family. Structurally similar compounds are those compounds which share the following structure:

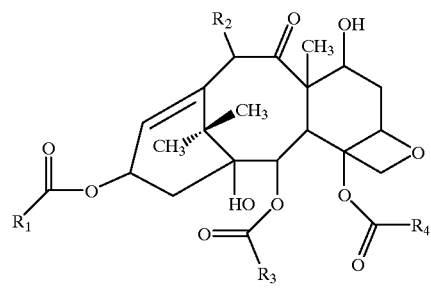

where:

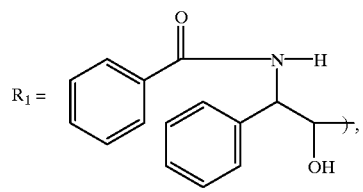

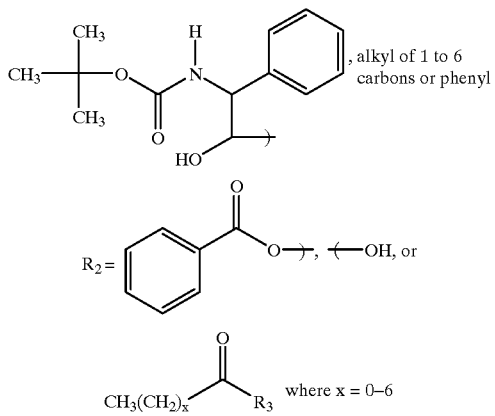

R₃=alkyl of 1 to 6 carbons or phenyl
R₄=alkyl of 1 to 6 carbons or phenyl

Examples of anti-neoplastic compounds, used herein, include paclitaxel and docetaxel. The preferred drug in accordance with the present invention is paclitaxel.

As used herein, "a dispersing/solubilizing agent" refers to those compounds capable of dispersing or solubilizing the anti-neoplastic compounds in alcoholic or aqueous media. Dispersing/solubilizing agents are able to act in this way because of the hydrophobic and hydrophilic groups present in the dispersing/solubilizing agents. Specifically, the hydrophobic groups interact with the hydrophobic anti-neoplastic compound while the hydrophilic groups interact with water. This behavior leads to enhanced solubility of the anti-neoplastic compound in aqueous systems. Examples of suitable dispersing/solubilizing agents include polyoxyethylated castor oils, and polyoxyethylene sorbitan esters. "Polyoxyethylated castor oil" is used herein to describe castor oil products capable of solubilizing and dispersing anti-neoplastic compounds. Polyoxyethylated castor oil products are produced by condensation of castor oil with ethylene oxide. Examples of preferred commercially available polyoxyethylated castor oil products are available under the trade-names Cremophor EL and Cremaphor EL-P. These products are readily available through BASF in Germany. Cremaphor EL may be prepared by the method disclosed in U.S. Pat. No. 3,070,499, incorporated herein by reference. Typically, the polyoxyethylated castor oil in accordance with the present invention is present as a 50% (V/V) solution with ethyl alcohol. "Polyoxyethylene sorbitan ester" is used herein to describe esters of sorbitol and its anhydrides which have been copolymerized with ethylene oxide. Common commercially available polyoxyethylene sorbitan esters are available under the trade-names Polysorbate 20, NF, Polysorbate 40, NF, Polysorbate 60, NF, and Polysorbate 80, NF. These products are readily available through ICI Americas in Wilmington, Del. Typically, the polyoxyethylene sorbitan ester, in accordance with the present invention, is used as a neat solution containing the anti-neoplastic compound. The most preferred solubilizing/dispersing agents are polyoxyethylated castor oils.

"Anti-oxidant" is used herein to describe any compound which is oxidized more easily than the anti-neoplastic compounds of the current invention. Without the use of an anti-oxidant, the oxidizing agents present (i.e., residual polymerization initiator, residual ethylene oxide, metal ions, etc.) in the solubilizing/dispersing agents tend to react with the anti-neoplastic compounds to cause degradation of the anti-neoplastic compound, and, as a result, a loss in long-term stability of the injectable finished formulation. The addition of an anti-oxidant to the solubilizing/dispersing agent inhibits anti-neoplastic degradation because the anti-oxidant reduces the oxidizing agents present in these solubilizing/dispersing agents or in any residual materials present with said solubilizing/dispersing agents as a result of manufacturing. Anti-oxidants can be added to the solubilizing/dispersing agent either as an aqueous solution or as a solid, depending on the solubility of the anti-oxidant. A stabilizing amount of an anti-oxidant would be any amount which reduces the amount of at least one impurity, and preferably the amount of the total impurities, in the pharmaceutical composition. Desirably, the amount of the impurity is reduced by at least 10%, preferably by at least 20–30%, and most preferably by at least about 50%. Water soluble anti-oxidants are preferred and should be added to the solubilizing/dispersing agent as a 2.0% to 67.0% (w/w) aqueous solution yielding final formulation concentrations in the range of 0.01% to 1.0% (w/w). Water soluble anti-oxidants are sodium metabisulfite, sodium bisulfite, sodium sulfite, dextrose, phenols, and thiophenols. The preferred anti-oxidant is an aqueous solution of sodium metabisulfite.

The pharmaceutical compositions of the invention can be prepared using conventional pharmaceutical batch tanks, filters, holding vessels, and vials. Specifically, a 1:1 ratio of solubilizing agent and dehydrated alcohol is prepared in a batch tank. A solution of sodium metabisulfite, or other soluble anti-oxidant, is prepared in a side mix, added to the batch tank containing the dehydrated alcohol and solubilizing agent, and mixed. The anti-neoplastic compound then is added to the batch tank and mixed with the above-mentioned ingredients, then the resulting solution is filtered through a 0.22 μm sterilizing filter into a sterile holding vessel. The sterile solution is then aseptically filled into sterile vials.

Typically, the anti-neoplastic compound in accordance with the present invention is provided, as a finished injectable solution, in a concentration ranging from between about 6 mg/mL to about 40 mg/mL. The most preferred concentration is 6mg/ml of paclitaxel.

Typically, the solubilizing/dispersing agent according to the present invention is provided in a concentration ranging from between about 40% to about 100% by volume as a homogeneous solution in dehydrated alcohol as appropriate. The most preferred concentration is between about 40% to about 70% by volume provided as a homogeneous solution in dehydrated alcohol.

Typically, the anti-oxidant in accordance with the present invention is provided in a concentration ranging from about 0.01%(w/w) to about 1%(w/w) of the finished injectable solution. The most preferred concentration ranges from between 0.01%(w/w) and 0.5%(w/w) of the finished injectable solution, respectively.

Pharmaceutical compositions according to the present invention are supplied as a nonaqueous solution intended for dilution with a suitable parenteral fluid prior to intravenous infusion. The pharmaceuticals are generally available in 30 mg (5 ml) and 100 mg (16.7 ml) multidose vials. Intravenous infusions are typically 135 to 175 mg/m² over a period of 3 to 24 hours. The pharmaceuticals are used after failure of first-line or subsequent chemotherapy for the treatment of metastatic carcinoma, especially ovarian and breast carcinoma.

The following examples further illustrate the invention and are not to be construed to limit the claims in any manner.

EXAMPLE 1

66.25 grams of Sterile Water for Injection, USP were placed into a clean, dry 250 ml glass beaker. 1.325 grams of sodium metabisulfite, NF were added to the Sterile Water for Injection, USP and mixed for a minimum of 10 minutes or until dissolved. This solution was covered and set aside for later use.

7,501 grams of Cremophor EL-P were placed into a 19 liter glass carboy. 5,596 grams of Dehydrated Alcohol, USP were added to the Cremophor EL-P and mixed for a minimum of 10 minutes or until homogeneously dispersed. The headspace of the carboy was flushed with filtered Nitrogen, NF while mixing. The sodium metabisulfite solution was added to the Cremophor EL-P and Dehydrated Alcohol mixture and mixed for a minimum of 10 minutes or until homogeneously dispersed. The carboy headspace was continued to be flushed with filtered Nitrogen, NF. 85.3 grams of paclitaxel were added and mixed for a minimum of 10 minutes or until completely dissolved. The final solution weight was adjusted to 13,250 grams with Dehydrated Alcohol, NF and mixed thoroughly. This final solution was aseptically filled into 5 ml unit vials.

TABLE I

Comparative Stability Study of Taxol ® and an Anti-Oxidant Stabilized Formulation According to Example 1 Stored at 40° C./75% Relative Humidity

| Product/ Condition | Potency (%) | Impurities (%) | | | |
|---|---|---|---|---|---|
| | | BAC III[a] | 10-DAT[b] | 7-Epi-Taxol | Total Impurities |
| Taxol ® Initial Test | 101.5 | 0.02 | 0.16 | — | 0.44 |
| Anti-Oxidant Stabilized Formulation Initial Test | 98.6 | 0.02 | 0.08 | — | 0.23 |
| Taxol ® 3 months | 100.5 | 0.05 | 0.35 | 0.17 | 0.70 |
| Anti-Oxidant Stabilized Formulation 3 months | 98.4 | 0.06 | 0.06 | — | 0.15 |
| Taxol ® 6 months | 99.1 | 0.09 | 0.53 | 0.27 | 1.13 |
| Anti-Oxidant Stabilized Formulation 6 months | 99.5 | 0.08 | 0.10 | 0.03 | 0.24 |

[a]BAC III = Baccatin III
[b]10-DAT = 10-Deacetyl Taxol

Table 1 provides a comparative compilation of stability data generated for storage of Taxol®, a commercially available product containing paclitaxel, and an anti-oxidant stabilized formulation made according to Example 1. These products were stored at 40° C./75% relative humidity for a period of six (6) months. Samples of these different formulations were analyzed for impurity levels. Evaluation of the impurity profiles for these products demonstrates that the anti-oxidant stabilized formulation yields an impurity profile with a lower overall total impurities content compared to Taxol®.

EXAMPLE 2

In an injectible container, 1.8 grams of paclitaxel were mixed with 150 ml of Dehydrated Alcohol and stirred to dissolve. 150 ml of Polyethylene Glycol 400 then were added and stirred to dissolve. 50.0 ml of an aqueous 0.05% Thiophenol solution then were added and stirred vigorously to assure complete solution.

EXAMPLE 3

Procedures similar to those of Examples 1 and 2 were followed for an array of different solubilizing/dispersing agents and anti-oxidants. Table II summarizes the combinations of solublilizing/dispersing agents and anti-oxidants used and the resulting compositions's stability.

Each of the formulations in Table II were prepared on a laboratory scale and then exposed to a thermal environment held at 105° C. for a period of five (5) hours. The samples then were analyzed for impurity levels and were compared to heated (i.e., 105° C. for five (5) hours) control sample preparations which did not contain an anti-oxidant. The formulations contained approximately 50% (V/V) of solubilizing/dispersing agent homogeneously mixed with ethanol. The anti-oxidants were added at levels ranging from 0.01% to 0.05% (W/W).

TABLE II

Use of Anti-Oxidants with Paclitaxel in Different Injectable Vehicles.

| Solubilizing or dispersing agent/ Anti-oxidant/Condition | Impurities (%) | | | |
|---|---|---|---|---|
| | BAC III[a] | 10-DAT[b] | 7-Epi-Taxol | Total Impurities |
| Cremophor EL-P/None/ 105° C. | 3.43 | 0.29 | 0.20 | 4.81 |
| Cremophor EL-P/0.05% Thiophenol/105° C. | 1.13 | 0.27 | 0.17 | 3.05 |
| Cremophor EL-P/0.05% Dextrose/105° C. | 2.98 | 0.28 | 0.15 | 4.30 |
| Cremophor EL-P/0.01% Sodium metabisulfite/ 105° C. | 0.04 | 0.16 | 0.16 | 0.84 |
| Polysorbate 80/None/ 105° C. | 18.39 | 1.33 | 2.83 | 32.91 |
| Polysorbate 80/0.05% Thiophenol/105° C. | 16.98 | 0.85 | 1.66 | 30.98 |
| Polysorbate 80/0.05% Dextrose/105° C. | 19.25 | 1.21 | 1.99 | 33.28 |
| Polysorbate 80/0.01% Sodium metabisulfite/ 105° C. | 16.78 | 0.92 | 1.25 | 27.14 |

[a]BAC III = Baccatin III
[b]10-DAT = 10-Deacetyl Taxol

The results in Table II demonstrate that the stabilizing action of the anti-oxidant component is dependent upon two factors: (i) the ease of oxidation of the anti-oxidant and (ii) the properties of the solubilizing/dispersing agent used in the formulation. In all cases presented in Table II, sodium metabisulfite demonstrates the greatest potential for formulation stability. Addition of thiophenol to the formulation yields enhanced stability in the Cremophor and Polysorbate 80 mixtures when compared to the appropriate control samples. Thiophenol appears to be less effective than sodium metabisulfite which is most likely due to thiophenol being somewhat more difficult to oxidize than sodium metabisulfite. Finally, dextrose demonstrates an overall stabilizing effect only in the Cremophor formulations, although it did reduce the concentration of one of the impurities in the polysorbate composition.

What is claimed:

1. A method for stabilizing a solubilizing/dispersing agent selected from the group consisting of polyoxyethylated castor oil, polyethylene glycol, and a polyoxyethylene sorbitan ester, which is to be added to an injectable taxoid-containing anti-neoplastic pharmaceutical composition, comprising adding an antioxidant to said agent prior to incorporating said agent into said composition and prior to dilution of said composition with a parenteral fluid, in an amount effective to increase the long-term storage stability of said undiluted composition following addition of said agent thereto, as compared to an otherwise identical composition which does not contain said antioxidant.

2. The method of claim 1, wherein said solubilizing/dispersing agent contains at least one oxidizing agent present as a result of the manufacture of said solubilizing/dispersing agent.

3. The method of claim 1, wherein said anti-oxidant is a compound which reduces the amount of at least one impurity in the pharmaceutical composition by at least ten percent (10%) before dilution with a parenteral fluid.

4. The method of claim 1, wherein said anti-oxidant is sodium metabisulfite, sodium sulfite, sodium bisulfite, dextrose, a phenol, a thiophenol, or a combination thereof.

5. The method of claim 1, wherein said anti-oxidant is added to said solubilizing/dispersing agent as a 2% to 67% (w/w) aqueous solution.

* * * * *